United States Patent [19]

Barrett

[11] Patent Number: 5,302,980
[45] Date of Patent: Apr. 12, 1994

[54] LENS USEFUL AS A KERATOSCOPE

[76] Inventor: Graham D. Barrett, 56 Dampier Avenue, City Beach, Western Australia, Australia, 6015

[21] Appl. No.: 768,194
[22] PCT Filed: Apr. 17, 1990
[86] PCT No.: PCT/AU90/00148
    § 371 Date: Oct. 11, 1991
    § 102(e) Date: Oct. 11, 1991
[87] PCT Pub. No.: WO90/12533
    PCT Pub. Date: Nov. 1, 1990

[30] Foreign Application Priority Data

Apr. 14, 1989 [AU] Australia .............. PJ3670

[51] Int. Cl.⁵ .............................. A61B 3/10
[52] U.S. Cl. ...................... 351/212; 351/247; 359/711
[58] Field of Search ............ 351/211, 212, 217, 247; 359/364, 365, 369, 711, 724

[56] References Cited

U.S. PATENT DOCUMENTS

| | | | |
|---|---|---|---|
| 2,949,819 | 8/1960 | Smith | 88/57 |
| 3,781,097 | 12/1973 | Bechtold | 351/167 |
| 4,157,859 | 6/1979 | Terry | 350/35 |
| 4,172,639 | 10/1979 | Lang et al. | 351/13 |
| 4,256,385 | 3/1981 | Cohen et al. | 351/13 |
| 4,426,141 | 1/1984 | Holcomb | 351/212 |
| 4,491,398 | 1/1985 | Karickhoff | 351/211 |
| 4,660,946 | 4/1987 | Nakamura et al. | 351/212 |
| 4,772,115 | 9/1988 | Gersten et al. | 351/212 |
| 4,786,163 | 11/1988 | Imamichi et al. | 351/212 |
| 4,807,989 | 2/1989 | Nagano et al. | 351/212 |
| 5,009,498 | 4/1991 | Gersten et al. | 351/212 |
| 5,018,850 | 5/1991 | Gersten et al. | 351/212 |

FOREIGN PATENT DOCUMENTS 104615 8/1938 Australia .
138705 10/1981 Japan .

Primary Examiner—Bruce Y. Arnold
Assistant Examiner—Hung Xuan Dang
Attorney, Agent, or Firm—Kerkam, Stowell, Kondracki & Clarke

[57] ABSTRACT

A toroidal lens (10) or a plurality of such lenses attached to a handle (14) for use as or in a keratoscope (12). If a plurality of lenses are employed, they are arranged either in different planes parallel to each other or concentrically in a single plane with varying degrees of ellipticity.

7 Claims, 12 Drawing Sheets

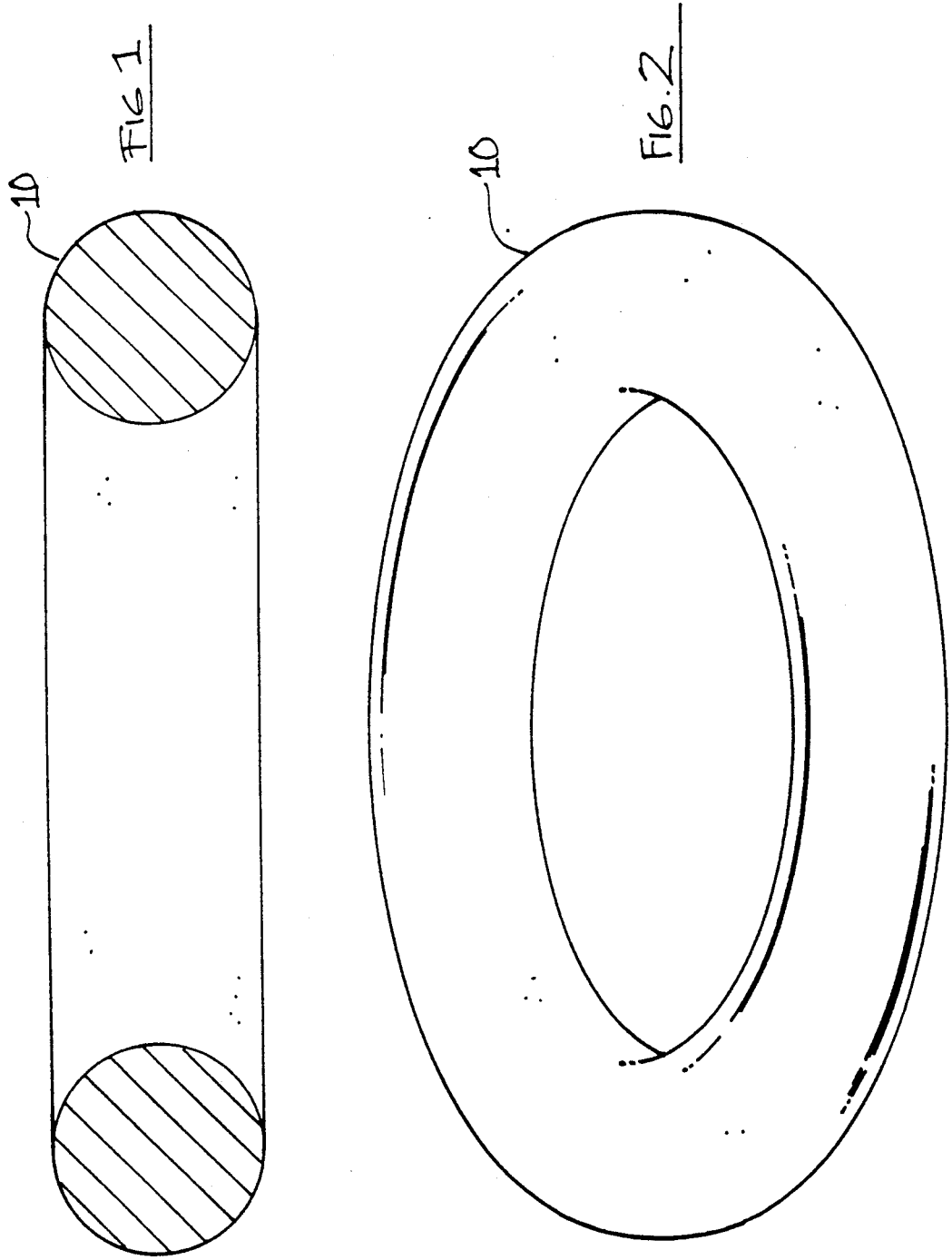

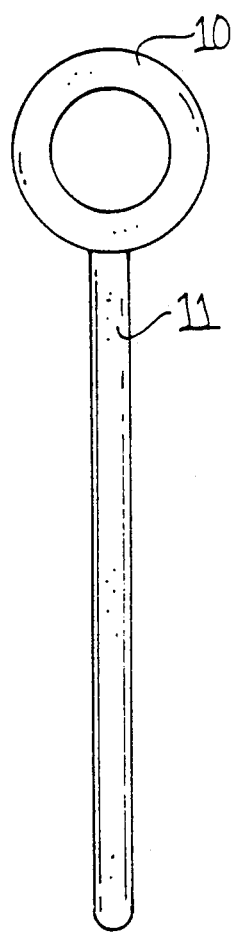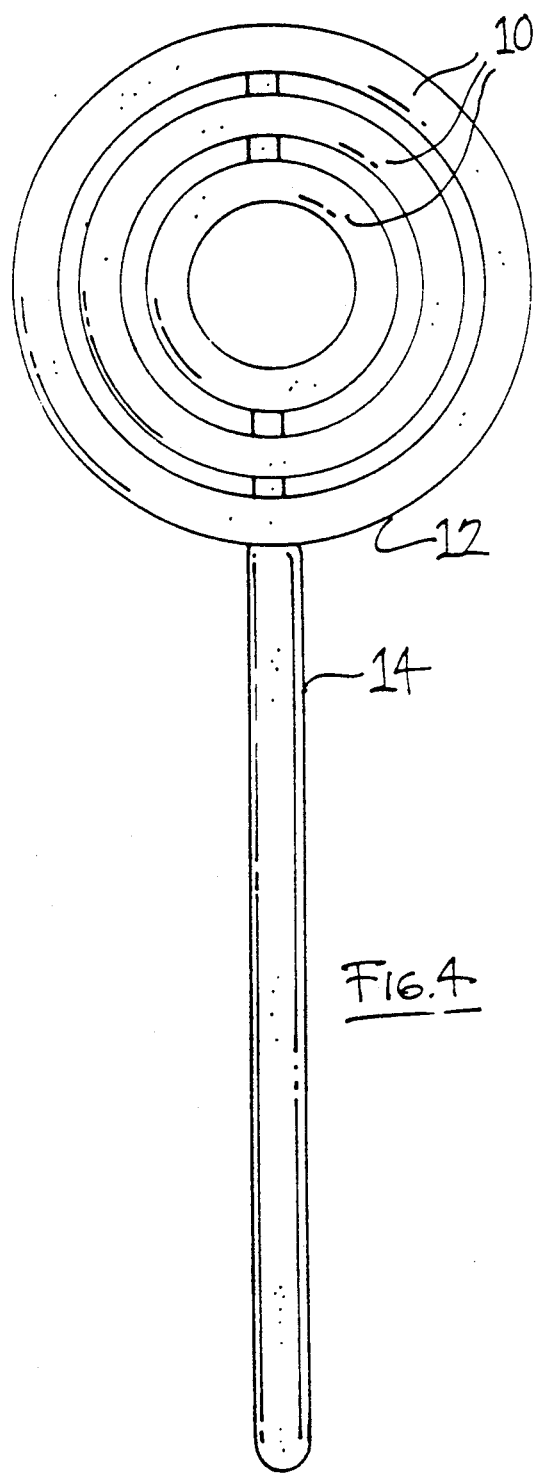

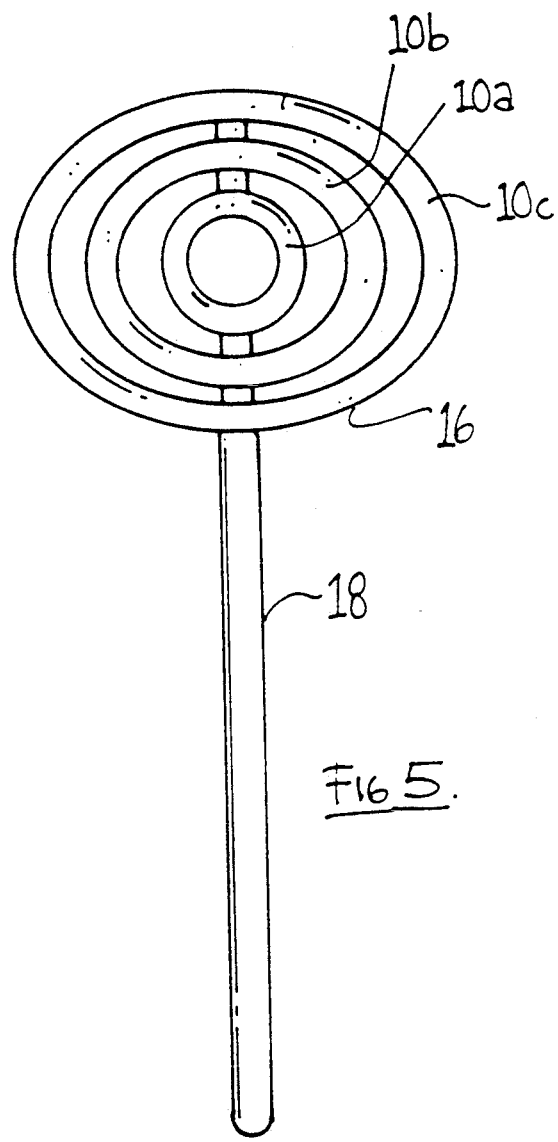

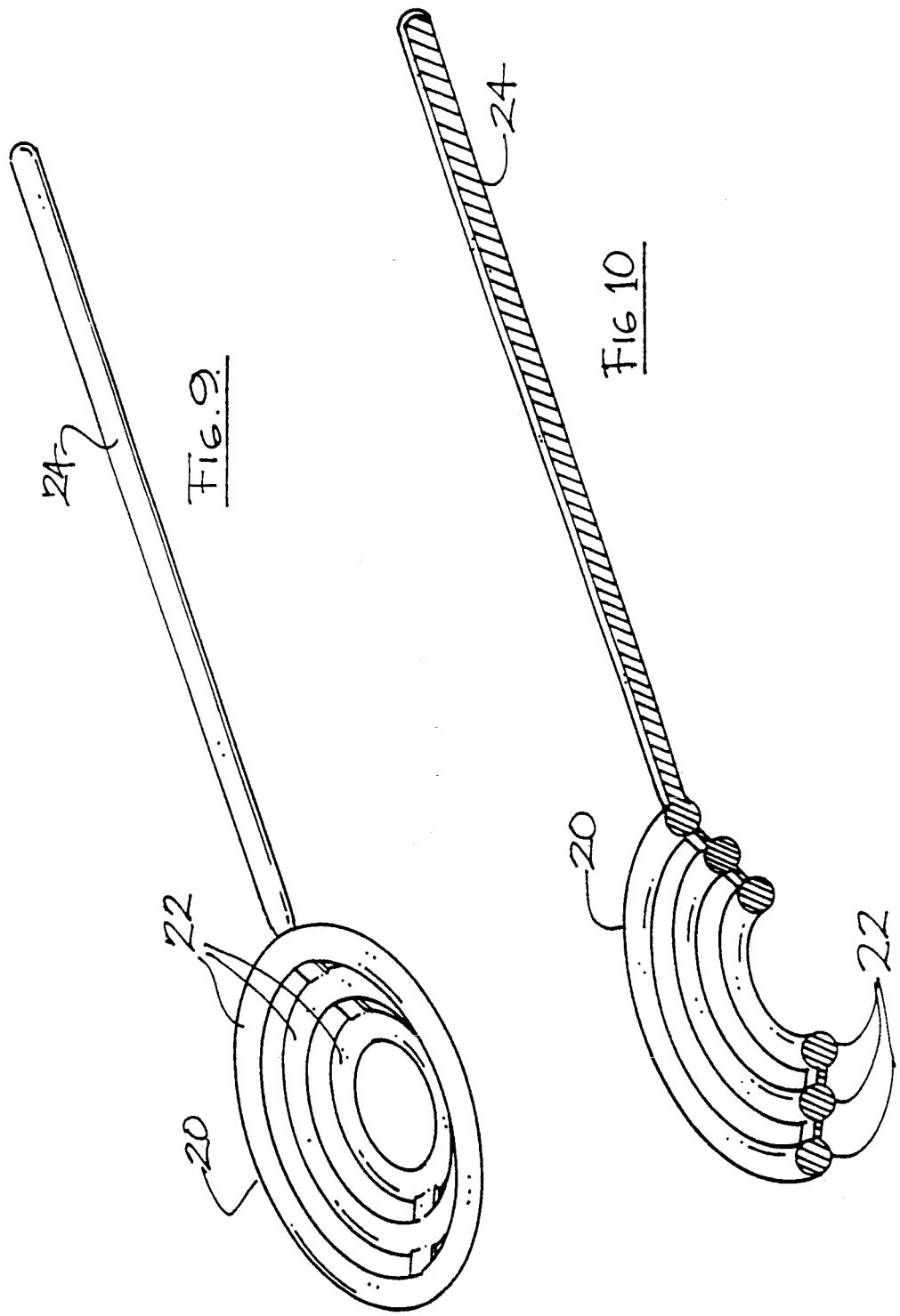

LENS USEFUL AS A KERATOSCOPE

DESCRIPTION

The present invention relates to a lens useful as a keratoscope.

BACKGROUND OF THE INVENTION

There are situations in which it is necessary to obtain an assessment of the degree of astigmatism of a cornea of an eye. For example, when a surgeon has made an incision in the cornea as part of an operating procedure such as insertion of an intraocular lens, it is necessary at the end of the procedure to close the incision by means of sutures. However, the sutures have to have an appropriate degree of tension to avoid inducing excessive stigmatism in the cornea. The lens of the present invention enables the surgeon to monitor readily the degree of astigmatism in a cornea as suturing is in progress and to adjust the tension of the sutures if necessary.

For example, closure of the surgical wound following cataract extraction and intraocular lens implantation may result in significant postoperative astigmatism. The amount of astigmatism is often unpredictable and may be a major factor limiting visual recovery and the final result of the procedure.

As surgical techniques and lens design have improved, other more serious complications have reduced in frequency. Patients' expectations have also increased and an excellent visual result following surgery is considered one in which patients not only have good corrected acuity, but are also able to see well without spectacles. The major problem which prevents ophthalmic surgeons from obtaining such a result is often the presence of surgically induced astigmatism. The introduction of multifocal and bifocal implants is another factor suggesting that levels of astigmatism previously considered routine may no longer be acceptable. At a recent conference (EIIC 1988) in Copenhagen, a panel of experts uniformly agreed that surgically induced astigmatism was the major remaining problem with their surgery over which they had inadequate control. This is one of the reasons why phacoemulsification and small incision cataract surgery is being considered by an increasing number of surgeons.

Even with these advanced techniques, astigmatism can still be a problem if wound closure and suture tension is not carefully monitored. Surgical Keratometers have been introduced to enable surgeons to monitor the corneal astigmatism during wound closure and adjust suture tension accordingly. These instruments have varied from complex and expensive instruments such as the Terry Keratometer to simple metal or plastic devices such as the Karickoff device which reflect a circle of light on the cornea. All these devices operate in a similar principle in that the reflected image of a circular light source will have an elliptical shape if significant astigmatism is present. More expensive instruments use incandescent or fibreoptic light sources to provide a bright image whilst the cheaper qualitative keratometers use reflected light from a metal or plastic circle. Unfortunately, the brightness of the corneal image with the qualitative keratometers is inadequate and the reflection is difficult to recognise. These qualitative keratoscopes have to be held at just the right angle to produce an image which is often difficult to recognise. The more expensive Keratometers produce adequate images, but are complex and time consuming. This has restricted their use to a small number of surgeons. The lens of the present invention is relatively inexpensive to produce compared to known qualitative Keratoscopes whilst providing a relatively bright reflected corneal image compared to known qualitative Keratoscopes.

SUMMARY OF THE INVENTION

In accordance with one aspect of the present invention, there is provided a lens useful as a keratoscope which is a light transmitting lens of annular shape with a toroidal surface.

Preferably, the annular light transmitting lens is of circular or semi-circular profile in cross-section.

BRIEF DESCRIPTION OF THE DRAWINGS

The present invention will now be described, by way of example, with reference to the accompanying drawings, in which:

FIG. 1 is a sectional view of a toroidal lens of circular cross-section useful as a keratoscope in accordance with the present invention;

FIG. 2 is a perspective view of the toroidal lens of FIG. 1;

FIG. 3 is a plan view of a hand-held keratoscope using the lens of FIGS. 1 and 2;

FIG. 4 is a plan view of a hand-held keratoscope including a plurality of the lenses of FIGS. 1 and 2 with all of the lenses being in a single plane;

FIG. 5 is a plan view of a keratoscope similar to FIG. 4 except that middle and outer lenses are of elliptical shape;

FIG. 9 is a perspective view of a keratoscope having a plurality of lenses similar to that shown in FIG. 4, except that the lenses are in different planes;

FIG. 10 is a sectional view through the keratoscope of FIG. 9 to show the cross-sectional profile and disposition of the lens;

DESCRIPTION OF THE INVENTION

In FIGS. 1 and 2, there is shown a toroidal lens 10 useful as a keratoscope which is of a shape formed by rotating a circle about a line in its plane but not intersecting it. Thus, the toroidal lens is circular in cross-section as shown in FIG. 1, but forms a closed ring or annulus as shown in FIG. 2.

The lens 10 is formed of light transmitting material such as plastics material or glass.

Figure 1A:
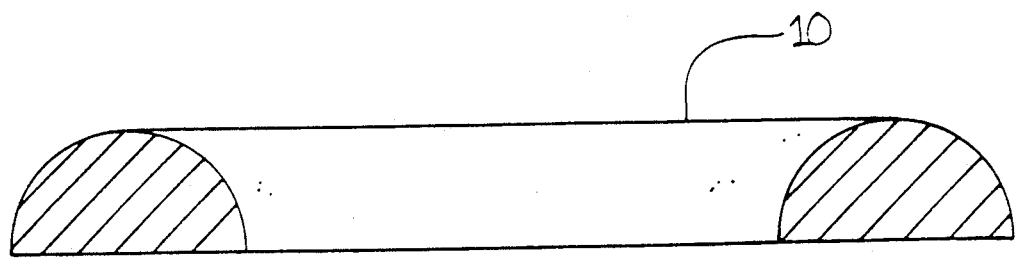
FIG. 1a is a sectional view of a toroidal lens of semi-circular cross-section useful as a keratoscope in accordance with the present invention.

Whilst the toroidal lens of FIGS. 1 and 2 has a body of circular profile in cross-section, it is envisaged that the body of the lens 10 could have other profiles. For example, the lens 10 could be of semi-circular profile in cross-section as shown in FIG. 1a.

The lens 10 can be used as a keratoscope by placing the lens between a source of light and an eye of a subject. The lens 10 produces a focused circular light image which is reflected from the corneal surface of the eye. If the cornea is completely spherical, then the reflected image will be circular. However, if the cornea is not completely spherical and shows significant astigmatism, the reflected image will have an elliptical shape.

Conveniently, as shown in FIG. 3, the lens 10 may be incorporated in a keratoscope 12 having a handle 11 attached to the lens 10 to enable the lens 10 to be manually manipulated and moved relative to the eye being observed. The position of the lens 10 relative to the cornea is not critical for obtaining a reflected image. An image will be obtained in a large range of distances from the corneal surface. However, the size of the reflected image will vary with the distance of the lens from the corneal surface.

Conveniently, the lens 10 is used in conjunction with a microscope which also provides a source of light to enable an operator to view the reflected image in the eye piece of the microscope. In this connection, the lens 10 is placed between the objective lens and the eye and focuses the co-axial light from the microscope.

In FIG. 4, there is shown a keratoscope 12 comprising a handle 14 and three concentric circular toroidal lenses 10 of progressively increasing size disposed in a single plane. The lenses 10 are of the same general type as the lens of FIGS. 1 and 2.

The multiple toroidal lenses of the keratoscope 12 can be used to provide multiple nested images which are reflected from the corneal surface. Conveniently, the three rings of the keratoscope can be differently coloured for easier interpretation of the results obtained.

In FIG. 5, there is shown a keratoscope 16 comprising a handle 18 and three nested annular toroidal lenses 10a, 10b, 10c which are of progressively increasing size, respectively. The innermost lens 10a is circular, the intermediate lens 10b is slightly elliptical and the outer lens 10c is substantially elliptical. Whilst three lenses of progressively increasing ellipticity with increasing size have been shown, it is envisaged that more lenses of ever increasing size and ellipticity could be added to the apparatus of FIG. 5.

If the cornea is completely spherical, then the reflected image of the ring 10a will be circular. However, if the cornea is not completely spherical and shows significant astigmatism, the reflected image of the ring 10a will not appear circular, but will have an elliptical configuration. If the long axis of the elliptical rings of the keratoscope 16 are aligned with the short axis of the reflected elliptical image of the inner ring from the corneal surface, then an operator can obtain an estimation of the degree of astigmatism of the cornea. This orientation can be achieved simply by rotating the keratoscope 16 by means of the handle 18.

If the degree of astigmatism in the cornea being investigated is moderate, then the second reflected ring image from the lens 10b will appear circular.

Further, if the degree of astigmatism in the cornea being investigated is large, then the outer ring will appear closest to a circle. By varying the degree of ellipticity of the plurality of toroidal lens, it is possible to calibrate the degree of astigmatism.

Figure 6:
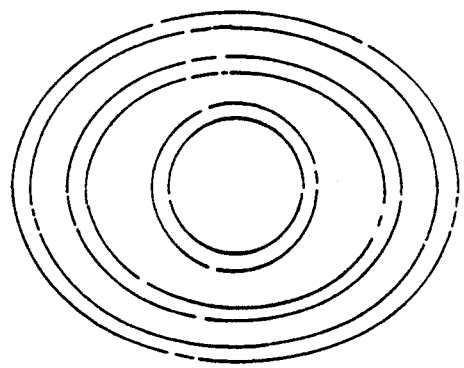
FIGS. 6 to 8 show reflected images obtained from surfaces having different degrees of asymmetry using the keratoscope of FIG. 5.
Figure 7:
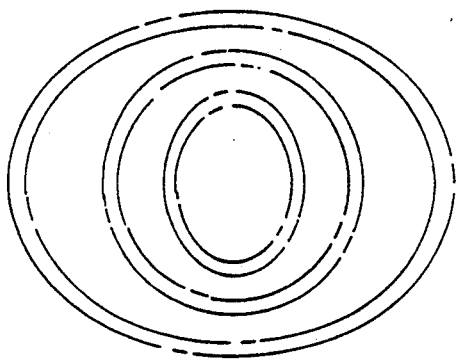

For example, in the reflected image of FIG. 6, the inner ring is completely circular which represents an image reflected from the lens 10a, is completely circular. This indicates a spherical cornea with little or no astigmatism. In FIG. 7, the middle ring is completely circular whilst the inner and outer rings are elliptical. This indicates an eye with a moderate degree of astigmatism of about 3 diopters. As can be seen in FIG. 7, the long axis of the ellipse of the inner ring is disposed at 90° to the long axis of the ellipse of the outer ring.

Figure 8:
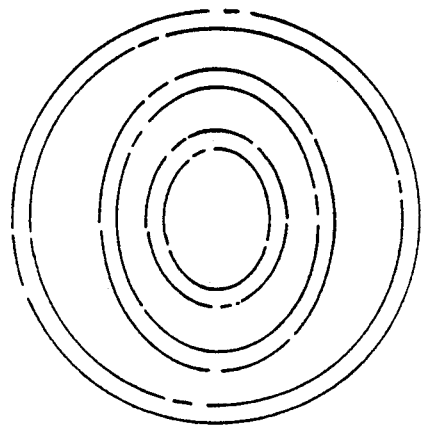

In FIG. 8, the outer ring is completely circular whilst the inner and middle rings are elliptical. This indicates an eye with a large degree of astigmatism of about 6 diopters. As can be seen in FIG. 8, the long axes of the ellipses of the inner and middle rings are disposed at 90° to the long axes of the ellipses of the middle and outer rings of FIG. 6.

The ellipticity of the outer rings could be changed from that shown in the drawings depending on the sensitivity of the keratoscope and the range of astigmatism desired to be measured.

In FIG. 9 there is shown a variation in the keratoscope 12 of FIG. 4. The keratoscope 20 shown in FIG. 9 has a plurality of concentric lenses 22 which are disposed in different planes, and a handle 24. As can best be seen in the transverse cross-section of FIG. 9 shown in FIG. 10, the lenses 22 are of progressively increasing size, but are located in different planes. In this way, the reflected images are of varying size depending on the distance of the lenses 22 from the eye. The lens 22 which is further from the eye has a correspondingly smaller image compared to lenses 22 which are closer to the eye.

The distance between the reflected rings mat therefor be adjusted by having the lenses in different planes. For example, a plurality of lenses in the same plane will produce reflected rings which may not be equidistant since the cornea is a curved reflecting surface. However, a plurality of lenses in different planes on an arc or curvature corresponding to that of the cornea will produce equidistant reflected rings. Alternatively, in some circumstances, it may be desired to invert the keratoscope of FIGS. 9 and 10 and have the smaller ring closest to the eye.

The construction shown in FIGS. 9 and 10 may conveniently be obtained by moulding a single piece of plastics material.

Figure 11:
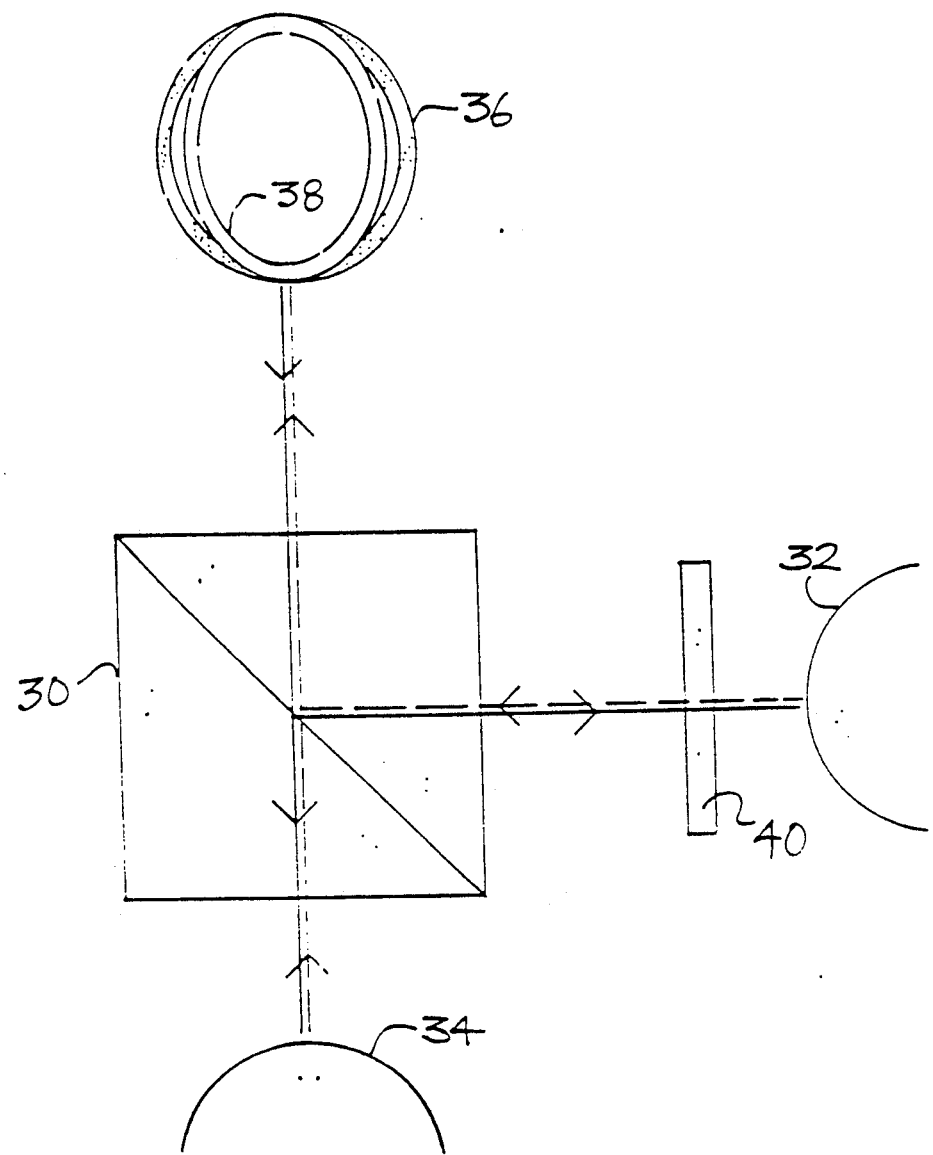
FIG. 11 is a schematic view of a beam splitter and reflector arrangement for use with the lens of the present invention.

In FIG. 11, there is shown an apparatus which provides a combination of a keratoscope ring produced using an apparatus in accordance with the present invention and a simultaneous circular image for comparison purposes. The apparatus of FIG. 11 comprises a beam splitter 30 and a convex or concave mirror or other reflective surface 32. The surface 32 has a radius of curvature which is the same as that of a cornea 34 when in a non-astigmatic state.

In use, the beam splitter 30 reflects some of the ring of incident light from a lens of the present invention through 90° to the surface 32. The surface 32 reflects this ring of light back to the beam splitter 30. Some of this ring of light reflected from the surface 32 which corresponds with a circular image 36 obtained from a non-astigmatic cornea is reflected back towards an eye of the operator. Simultaneously, some of the ring of incident light travels straight through the cornea 34 and is reflected straight back through the beam splitter 30. If the cornea 34 is astigmatic, a reflected keratoscopic image 38 from the cornea 34 will be elliptical as shown in FIG. 11. The elliptical image 38 reflecting from the cornea 34 and the circular image 36 reflected from the surface 32 are superimposed at the eye of the observer so that the observer can obtain an immediate comparison of the two reflected images 36 and 38 and thus assess the degree of astigmatism of the cornea 34. The use of a curved surface 32 enables the image 36 reflected therefrom to be of similar size to the keratoscope image 38 reflected from the cornea which assists in the comparison referred to. A colour filter 40 may be interposed between the beam splitter 30 and the surface 32 so that the reflected circular image 36 is differently coloured from the keratoscopic image 38 reflected from the cornea 34 to aid in the comparison.

Further, the surface 32 may be moveable away from and towards the beam splitter 30 and be mounted for this purpose on a calibrated micrometer (not shown). This enables the surface 32 to be moved in a calibrated manner relative to the beam splitter 30. The size of the reflected circular image 36 varies according to the distance of the surface 32 from the beam splitter 30. Thus, where the keratoscopic image 38 is elliptical the surface 32 can be moved to a position at which the circular image 36 has a diameter corresponding with the length of the long axis of the ellipse of the image 38. The calibration enables the operator to obtain an accurate measurement of the degree of ellipticity of the keratoscopic image 38 and thus the degree of astigmatism of the cornea 34.

Figure 12:
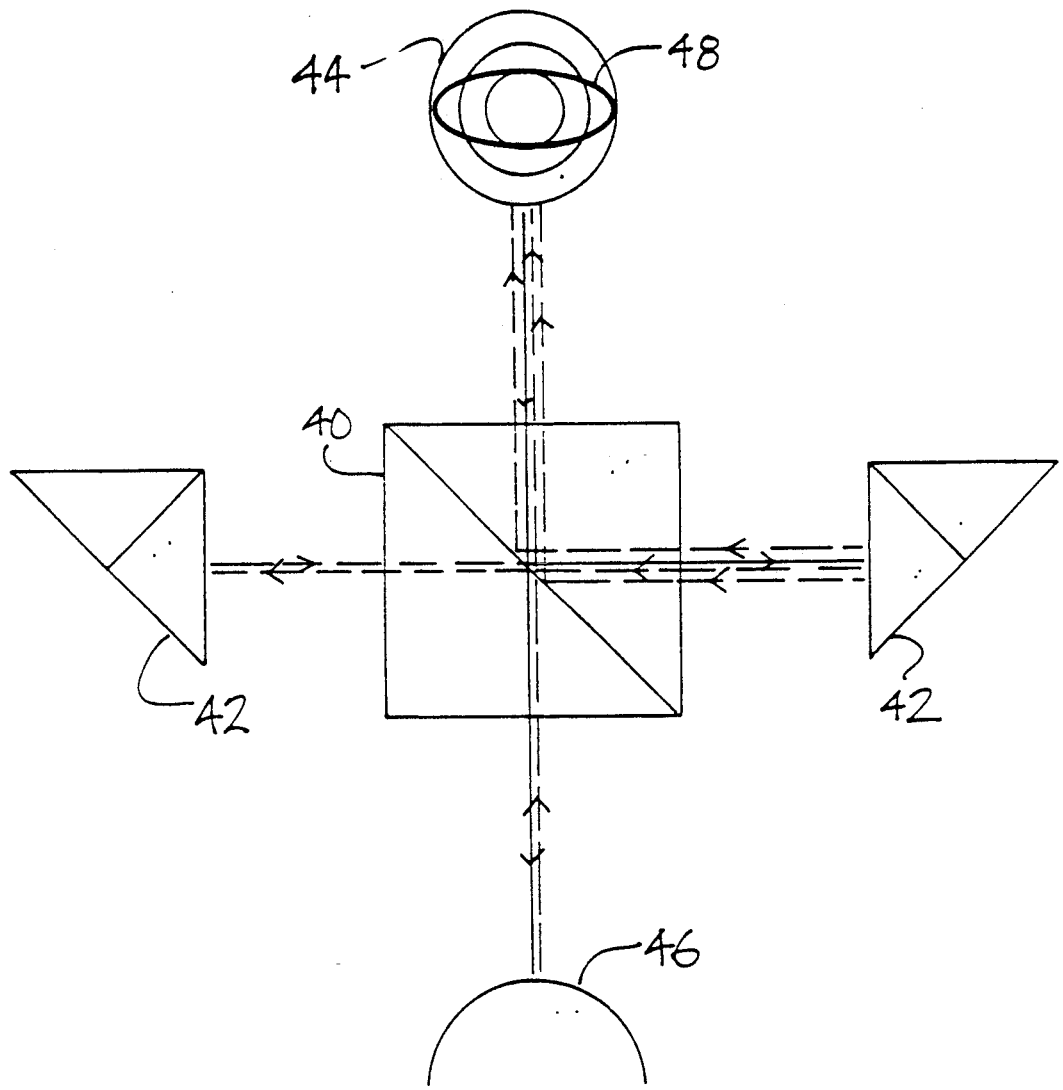
FIG. 12 is a schematic view of a beam splitter and multiple reflector arrangement for use with the lens of the present invention.

In FIG. 12, there is shown an apparatus which provides a combination of a keratoscopic image produced using an apparatus in accordance with the present invention and a plurality of simultaneous circular images for comparison purposes. The apparatus of FIG. 12 comprises a beam splitter 40 and a pair of opposed mirrors or retro reflective prisms 42 disposed on opposite sides of the beam splitter 40.

In use, the beam splitter 40 reflects some of the ring of incident light from the lens of the present invention to the reflecting member 42 on the right in FIG. 2. The light from the right-hand reflecting member 42 is reflected through the beam splitter 40, a number of times. At each pass through the beam splitter 40 some of the light is reflected back towards an eye of the observer. Further, the size of the reflected image ring diminishes with each pass so that reflected images that have been reflected a large number of times are smaller than images which have been reflected a lesser number of times. The result is that the observer sees a plurality of concentric rings 44 which are of circular shape. Further, some of the incident light will pass directly through the beam splitter 40 and be reflected from a cornea 46 straight back through the beam splitter 40 towards an eye of the observer. If the cornea 46 is astigmatic, the image 48 reflected from the cornea 46 will be elliptical as discussed above. The plurality of circular rings 44 of different size reflected from the reflecting members 42 enables a ready assessment of the degree of ellipticity of the image 48 to be made by the observer.

It is envisaged that the keratoscope of the present invention could be sold as part of a package for an intraocular lens as a major application of the keratoscope of the present invention lies in the closure of incisions made in the cornea after insertion of an intraocular lens in the eye.

Figure 13:
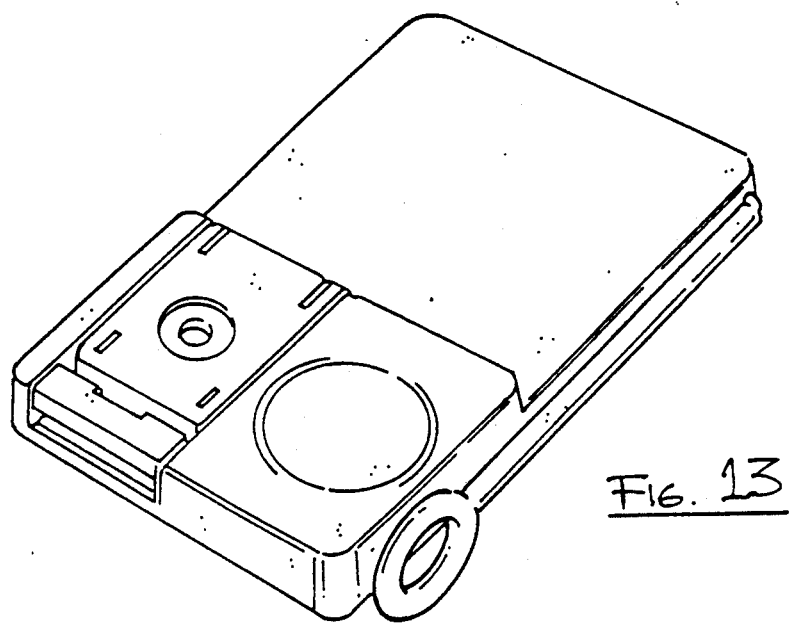
FIGS. 13 and 14 are views of the respective containers for intraocular lens having a keratoscope according to FIG. 3 releasably attached thereto.
Figure 14:
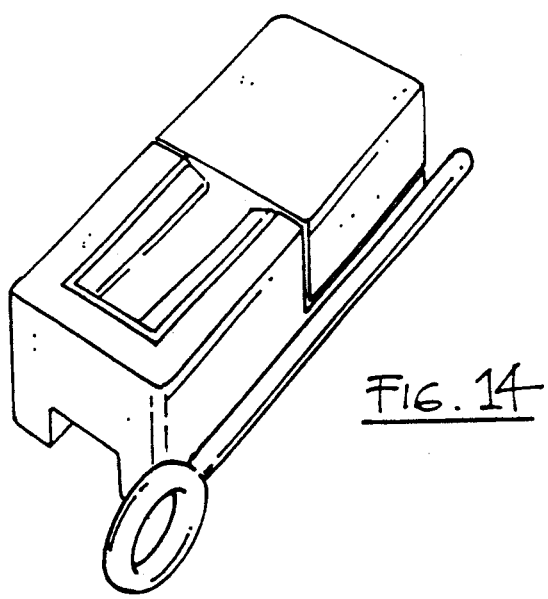

Typical packages for intraocular lens having keratoscopes in accordance with the present invention, frangibly attached thereto are shown in FIGS. 13 and 14. Further, it is envisaged that the keratoscope lens of the present invention could be formed with a package for an intraocular lens such as those shown in FIGS. 13 and 14, so that the package itself could be used as a keratoscope.

Figure 14A:
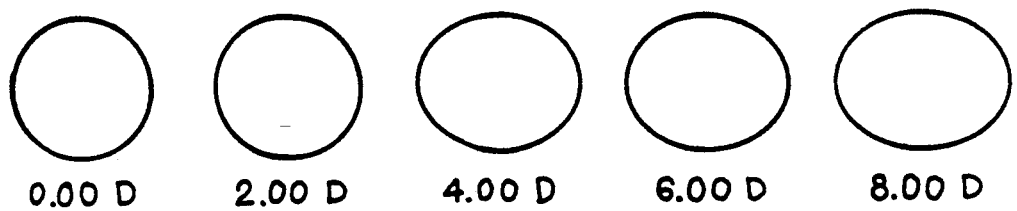
FIG. 14a is a plan view of a chart which can be used in conjunction with the lens of the present invention.

Further, in an alternative form of packaging, the keratoscope could be incorporated in a sterile, flexible feature package which incorporates a small chart with a number of images marked thereon. The images of the chart would be of varying degrees of ellipticity corresponding with degrees of astigmatism ranging from, for example, 0 diopters to 8.00 diopters as shown in FIG. 14a. Thus, this chart provides the observer with a ready guide as to the degree of ellipticity of a keratoscopic image reflected from a cornea and thus the degree of astigmatism of the cornea.

Further, when a surgeon has made an incision in an eye and has completed the surgical procedure, it is necessary to close the incision by means of sutures. It is important that the sutures be of the required degree of tension to avoid inducing an undesirable degree of astigmatism in the eye.

Figure 15:
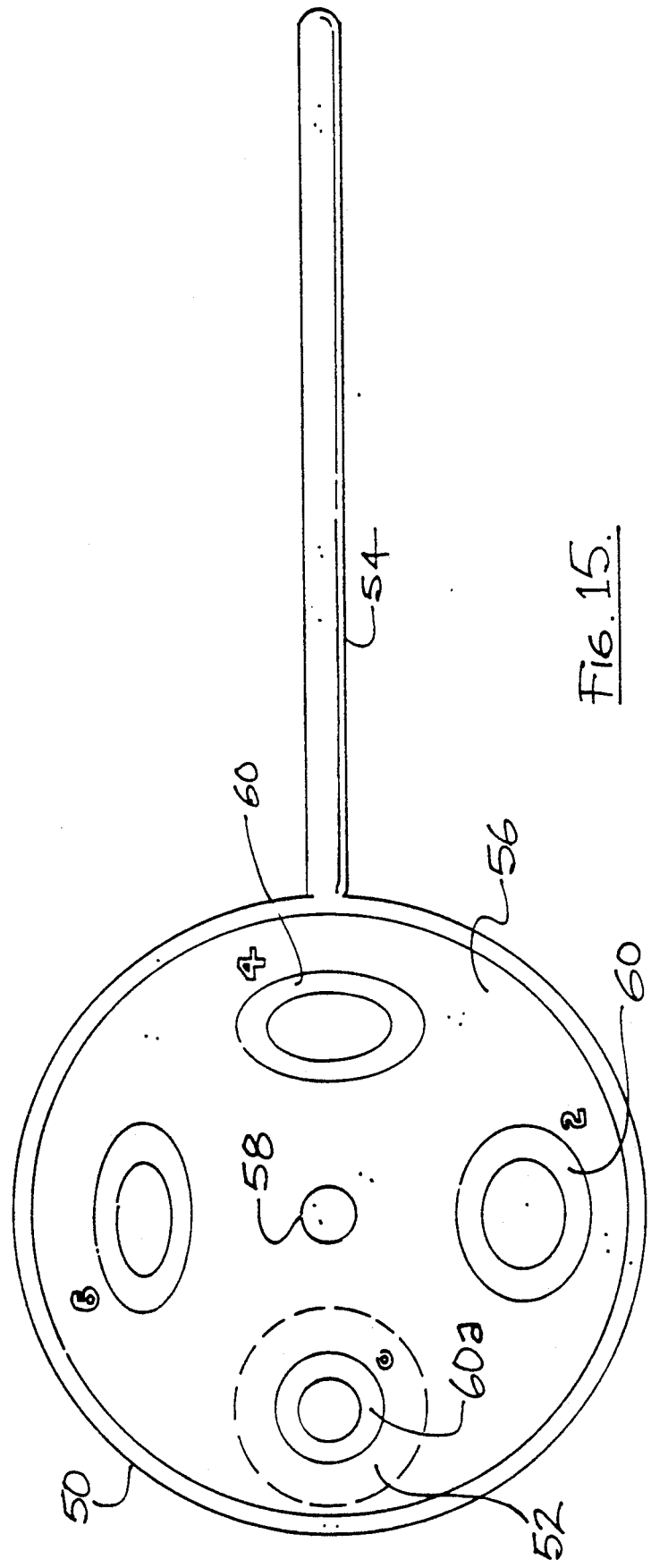
FIG. 15 is a plan view of a hand-held keratoscope incorporating a number of lenses in accordance with the present invention mounted on a rotatable member in a circle about the periphery thereof.

In FIG. 15 there is shown a further embodiment of the present invention which could be used during the suturing procedure to ensure that the sutures are at the appropriate degrees of tension so as to minimise the problem of excessive astigmatism.

The apparatus of FIG. 15 comprises an opaque base plate 50 having a viewing aperture 52 formed therein. A handle 54 is attached to the base plate 50. A rotatable transparent disc 56 is mounted to a pin 58 on the plate 50 such that the disc 56 is rotatable in a plane parallel to the plane of the plate 50. As shown, the disc 56 is formed with a plurality of toroidal lens 60 of varying degrees of ellipticity as indicated by the diopter number adjacent each lens 60. The disc 56 can be readily rotated manually by the surgeon so as to bring each lens 60 to the viewing aperture 52 in turn. If the lens 60 of greatest ellipticity in the viewing aperture 52 and an image thereof reflected from a cornea is substantially circular, the cornea has a high degree of astigmatization. Alternatively, if the image reflected from the lens 60a which is substantially circular, is also circular, then the cornea has little or no astigmatism. By rotating the disc 56, the surgeon can monitor continuously the degree of astigmatism of the cornea and adjust his sutures accordingly.

Figure 16:
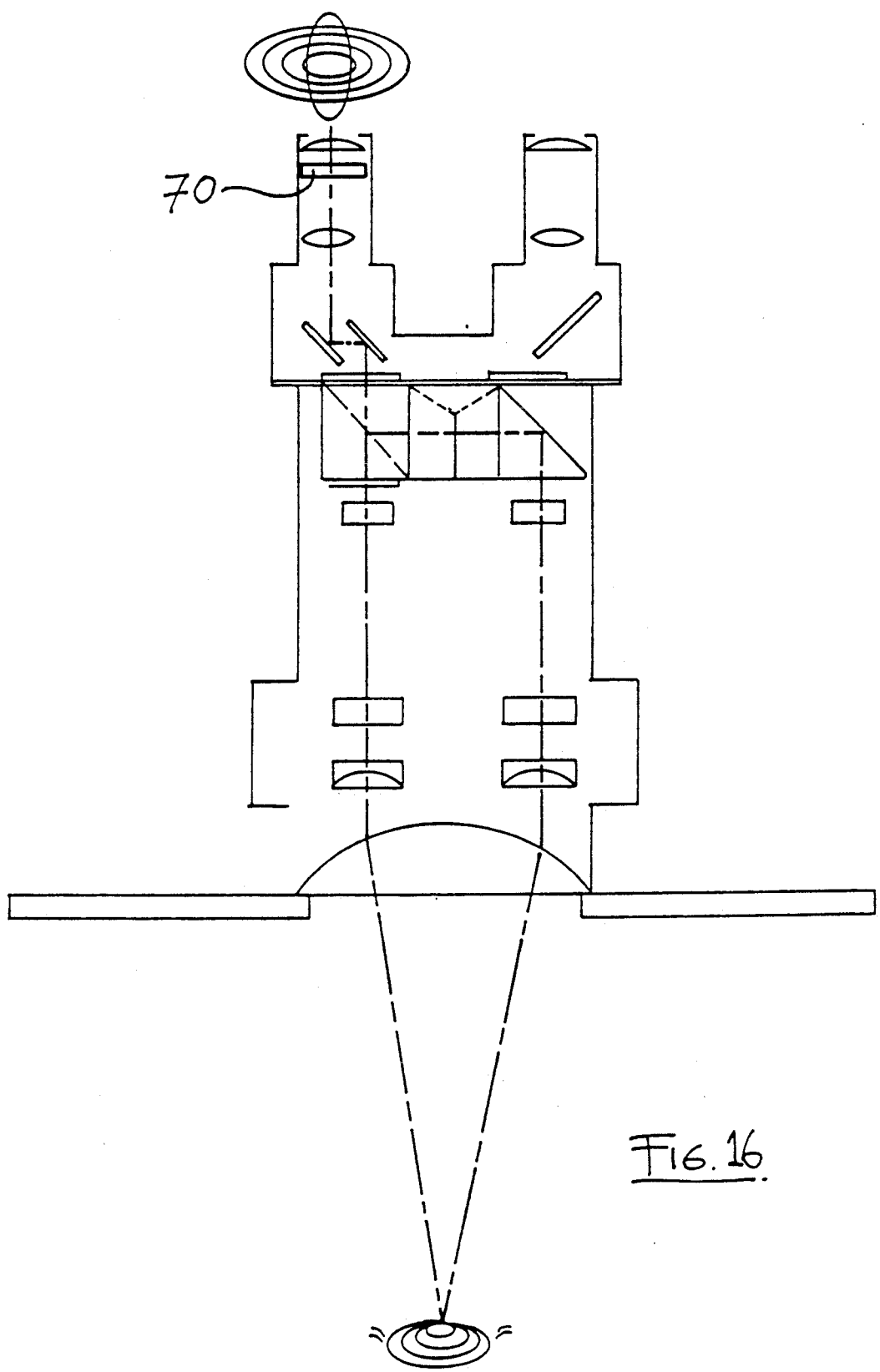
FIG. 16 is a schematic view of a binocular microscope incorporating a reticule in an eye piece for use in conjunction with the lens of the present invention.

Still further, it is envisaged that the keratoscope of the present invention could be used in conjunction with a microscope containing a reticule in the eye piece thereof. The reticule would typically comprise a number of concentric rings representative of differing degrees of astigmatism. The keratoscopic image reflected from the cornea is observable in the eye piece of the microscope in known manner and is superimposed on the image from the reticule. Thus, the observer can form an assessment of the degree of ellipticity of the reflected image by observing which ring of the reticule corresponds with the length of the long axis of an ellipse of the reflected image. The reticule could be illuminated or non-illuminated. A binocular microscope incorporating a reticule 70 is shown in FIG. 16.

Yet still further, it is envisaged that the apparatus of the present invention could be used in conjunction with a slit lamp. The slit lamp sold under Trade Mark "Rodenstock" has a retractable diffuser and can be used in conjunction with the keratoscope of the present invention without modification. However, other types such as that sold under the Trade Mark "Haag-Streit" may need to be provided with a diffusing element such as a piece of frosted plastics material or glass or a diffusing lens to provide a beam large enough to illuminate the whole of the lens of the keratoscope of the present invention.

The keratoscope of the present invention can be formed from plastics material or glass and can be formed by moulding techniques or by cutting techniques. Further, a glass keratoscope can be formed by bending an end of a molten glass rod to a circular shape and joining the free end to the rod.

Further, it is envisaged that a plastics material keratoscope in accordance with the present invention could incorporate ingredients which make the keratoscope biodegradable or photodegradable.

Modifications and variations such as would be apparent to a skilled addressee are deemed within the scope of the present invention.

What is claimed is:

1. A keratoscope which comprises a light transmitting lens which is of annular shape, has a toroidal surface and is disposed in a plane, wherein said lens is attached to a handle which extends away from said lens in a direction generally in alignment with the plane of said lens, and said lens and said handle are formed in one piece.

2. A keratoscope according to claim 1, characterized by comprising a plurality of the lenses of differing sizes.

3. A keratoscope according to claim 2, characterized in that the lenses are disposed in a single plane.

4. A keratoscope according to claim 2, characterized in that the lenses are disposed in different planes.

5. A keratoscope according claim 2, characterized in that the plurality of lenses are of varying degrees of ellipticity.

6. A keratoscope according to claim 1, characterized in that the keratoscope comprises an opaque base plate with a viewing aperture and a rotatable plate member to the base plate, wherein the rotatable plate is provided with a plurality of lenses arranged to be brought in them to the viewing aperture upon rotation of the rotatable member and being of varying ellipticity.

7. A lens useful as a keratoscope characterized in that the lens is of a circular or semi-circular shape and has a light transmitting lens of annular shape with a toroidal surface which is attached to a handle, the lens and handle being formed in one piece, the keratoscope being further characterized in that there is provided a beam splitter and a respective surface to provide a circular image for comparative purposes.

* * * * *